US008623347B2

(12) United States Patent
Dai et al.

(10) Patent No.: US 8,623,347 B2
(45) Date of Patent: Jan. 7, 2014

(54) ANTIVIRAL DRUGS FOR TREATMENT OF ARENAVIRUS INFECTION

(75) Inventors: Dongcheng Dai, Corvallis, OR (US); Dennis E. Hruby, Albany, OR (US); Tove C. Bolken, Keizer, OR (US); Sean M. Amberg, Corvallis, OR (US); Travis K. Warren, Middletown, MD (US)

(73) Assignee: Siga Technologies, Inc., Corvallis, OR (US)

( * ) Notice: Subject to any disclaimer, the term of this patent is extended or adjusted under 35 U.S.C. 154(b) by 0 days.

(21) Appl. No.: 12/735,392

(22) PCT Filed: Jan. 14, 2009

(86) PCT No.: PCT/US2009/030919
§ 371 (c)(1),
(2), (4) Date: Sep. 29, 2010

(87) PCT Pub. No.: WO2009/123776
PCT Pub. Date: Oct. 8, 2009

(65) Prior Publication Data
US 2011/0027227 A1 Feb. 3, 2011

Related U.S. Application Data

(60) Provisional application No. 61/006,457, filed on Jan. 15, 2008.

(51) Int. Cl.
| *A61K 9/02* | (2006.01) |
| *A61K 31/7056* | (2006.01) |
| *A61K 31/437* | (2006.01) |
| *A61K 31/4184* | (2006.01) |
| *A61K 31/675* | (2006.01) |
| *A61K 38/21* | (2006.01) |
| *A61K 39/00* | (2006.01) |

(52) U.S. Cl.
USPC ....... 424/85.4; 424/184.1; 514/303; 514/394; 514/43; 514/86; 546/118; 548/305.4

(58) Field of Classification Search
None
See application file for complete search history.

(56) References Cited

U.S. PATENT DOCUMENTS

| 5,958,910 A | 9/1999 | Cesura et al. |
| 2006/0293377 A1 | 12/2006 | Wizel et al. |
| 2007/0254934 A1 | 11/2007 | Hruby et al. |
| 2007/0275962 A1 | 11/2007 | Koul et al. |
| 2008/0300265 A1 | 12/2008 | Hruby et al. |

FOREIGN PATENT DOCUMENTS

| JP | 2010-500397 A | 1/2010 |
| WO | WO2008/020211 A2 | 2/2008 |
| WO | 2008041966 A2 | 4/2008 |

OTHER PUBLICATIONS

HemorrhagicFever, 2011, http://www.medicinenet.com/viral_hemorrhagic_fever/page4.htm.*
Dilk et al, caplus an 1998:364921.*
coxsackievirus, 2012, http://www.histopathology-india.net/coxsackievirus.htm.*
Garuti et al., II Farmaco, 55, 2000, 35-39.*
Stella J. P. et al., Characteristics of the in Vitro Inhibition of Arenavirus Synthesis by Bis-Benzimidazoles, Antimicrobial Agents and Chemotherapy, American Society for Microbiology, Washington DC, vol. 6, No. 6, Dec. 1, 1974, pp. 747-753.
European Search Report No. EP 09 72 7680, Dated Nov. 24, 2010.
Mode of Action and Biochemical Characterization of REP8839, a Novel Inhibitor of Methionyl-tRNA Synthetase, Ochsner et al., Antimicrobial Agents and Chemotherapy, Oct. 2005, p. 4253-4262, vol. 49, No. 10.
Adair, c. v., R. L. Gauld, and J. £. Smadel. 1953; Aseptic meningitis, a disease of diverse etiology: clinical and etiologic studies on 854 cases. Ann. Intern. Med. 39:675-704.
Buchmeier, M. J., M. D. Bowen, and C. J. Peters; 2001. Arenaviridae: the viruses and their replication, p. 1635-1668. In D. M. Knipe and P. M. Howley (ed.), Fields Virology, 4th ed. Lippincott, Williams and Wilkins, Philadelphia PA.
Fischer, S. A., M. B. Graham, M. J. Kuehnert, C. N. Kotton, A. Srinivasan, F. M. Marty, J. A. Comer, J. Guarner, C. D. paddock, D. L. DeMeo, W.-J. Shieh, B. R. Erickson, U. Bandy, A. DeMaria, Jr., J. P. Davis, F. L. Delmonico, B. Pavlin, A. Likos, M. J. Vincent, T. K. Sealy, C. S. Goldsmith, D. B. Jernigan, P. E. Rollin, M.M. packard, M. Patel, C. Rowland, R. F. Helfand, S. T. Nichol, J. A. Fishman, T. Ksiazek, S. R. Zaki, and the LCMV in Transplant Recipients Investigation Team 2006.
Lee, K. J., I. S. Novella, M. N. Teng, M. B. A. Oldatone, and J. C. de la Terre. 2000. NP and L proteins of lymphocytic choriomeningitis virus (LCMV) are sufficient for efficient transcription and replication of LCMV genomic RNA analogs. J. Viral. 74:3470-3477.
Meyer, H. M., Jr., R. T. Johnson, I. P. Crawford, H.E. Dascomb,and N. G. Rogers. 1960. Central nervous system syndromes of "vital" etiology. A study of 713 cases. Am.J. Med. 29:334-347.
NIAID. 2002. NIAID biodefense research agenda for CDC category A agents. NIH Publication No. 03-5306.
NIAID. 2007; NIAID category A, Band C priority pathogens. http://www3.niaid.nih.gov/biodefense/PDF/cat.pdf, accessed Dec. 6, 2007.
O'Brien, J., I. Wilson, T. Orton, and F. Pognan. 2000. Investigation of the Alamar Blue (resazurin) fluorescent dye for the assessment of mammalian cell cytotoxicity. Eur. J. Biochem. 267:5421-5426.
Oldstone, M. B. A. 2007. A suspenseful game of 'hide and seek' between virus and host. Nat. Immunol. 8:325-327.
Perez, M., R. C. Craven, and J. C. de la Torre. 2003; The small RING finger protein Z drives arenavi,us budding: implications for antiviral strategies. Proc. Natl. Acad. Sci. USA 100:12978-12983.

(Continued)

*Primary Examiner* — Sun Jae Loewe
(74) *Attorney, Agent, or Firm* — Kramer Levin Naftalis & Frankel LLP

(57) ABSTRACT

Compounds, methods and pharmaceutical compositions for treating viral infections, by administering certain compounds in therapeutically effective amounts are disclosed. Methods for preparing the compounds and methods of using the compounds and pharmaceutical compositions thereof are also disclosed. In particular, the treatment and prophylaxis of viral infections such as caused by the Arenavirus family is disclosed.

18 Claims, No Drawings

(56) References Cited

OTHER PUBLICATIONS

Peters, C. J. 2006. Lymphocytic choriomeningitis virus—an old enemy up to new tricks. N. Engl. J. Med. 354:2208-2211.

Rotz, L. D., A. S. Khan, S. R. Lillibridge, S. M. Ostroff, and J. M. Hughes. 2002. Public health assessment of potential bioterrorism agents. Emerg. Infect. Dis. 8:225-230.

Sanchez, A. B., and J. C. de la Torre. 2005. Genetic and biochemical evidence for an oligomeric structure of the functional L polymerase of the prototypic arenavirus lymphocytic choriomeningitis virus. J. Virol. 79:72627268.

Wright, R., D. Johnson, M. Neumann, T. G. Ksiazek, P. Rollin, R. V. KeeCh,. D. J. Bonthius, P. Hitchon, C. F.Grose, W. E. Bell, and J. F. Bale, Jr. 1997. Congenital lymphocytic choriomeningitis virus syndrome: a disease that mimics congenital toxoplasmosis or cytomegalovirus infection. Pediatrics lOO:e9.

International Search Report and Written Opinion issued for International Application No. PCT/US2009/30919, dated Aug. 27, 2009.

Oztekin Alkul et al., "Activity of Bisbenzimidazoles Derivative to *Staphylooccus* Epidermidis," Asian Journal of Chemistry, vol. 19, No. 4 (2007), 3145-3151.

Chemical Abstracts, 1989, 110(1), 419, 4510d10.

\* cited by examiner

ANTIVIRAL DRUGS FOR TREATMENT OF ARENAVIRUS INFECTION

CROSS REFERENCE TO RELATED APPLICATIONS

This application is the United States national phase filing of the corresponding international application number PCT/US2009/030919, filed on Jan. 14, 2009, which claims priority to and benefit of U.S. Application No. 61/006,457, filed Jan. 15, 2008, which applications are hereby incorporated by reference in their entirety.

STATEMENT REGARDING FEDERALLY SPONSORED RESEARCH OR DEVELOPMENT

This invention was made with U.S. Government support under Grant No. R43 AI056525 and Grant No. R44 AI056525, awarded by the National Institute of Health (NIH). The U.S. Government has certain rights in the invention.

FIELD OF THE INVENTION

This invention relates to the use of 2,2'-bibenzimidazole, 2,2'-bibenzoxazole and 2,2'-bibenzothiazole derivatives and analogs, as well as compositions containing the same, for the treatment or prophylaxis of viral diseases associated with the arenavirus family such as lymphocytic choriomeningitis virus (LCMV).

BACKGROUND OF THE INVENTION

LCMV is the prototypic member of the Arenaviridae family, a family of enveloped RNA viruses (2). Arenavirus infection in rodents, the natural host animal, is usually chronic and asymptomatic. Several arenaviruses can cause severe hemorrhagic fever in humans, including Lassa, Machupo, Guanarito, and Junín viruses. Transmission to humans can result from direct contact with infected rodents or their habitat, through aerosolized rodent secretions, or through contact with the body fluids of an infected person. LCMV is found world-wide, reflecting the range of the Mus musculus rodent host. The Arenaviridae family contains a single genus (*Arenavirus*) that is divided into two major lineages based on phylogenetic and serological examination. LCMV is a member of the Old World arenaviruses, which includes the Lassa fever virus, a Category A hemorrhagic fever virus.

In 1999, the Centers for Disease Control and Prevention (CDC) identified and categorized potential biological terrorism agents as part of a Congressional initiative to upgrade bioterrorism response capabilities (12). Arenaviruses were designated as Category A, defined as those pathogens with the highest potential impact on public health and safety, potential for large-scale dissemination, capability for civil disruption, and greatest unmet need for public health preparedness. The National Institute of Allergy and Infectious Diseases (NIAID) has continued to update the Category A list (6), specifically listing LCMV as a Category A virus (7).

Although LCMV is closely related to other arenaviruses known to cause hemorrhagic fever, LCMV has been linked to only a very limited number of cases in which patients exhibited hemorrhagic fever-like symptoms (11). More often, exposure to the virus results in a characteristic biphasic pattern of illness, beginning with flu-like symptoms characterized by fever, headache, myalgia, malaise, and fatigue after an incubation period of 1-3 weeks. Following a few days of recovery, a second phase of disease can occur in which patients exhibit symptoms of meningitis (fever, headache, or stiff neck) or encephalitis (drowsiness, confusion, sensory disturbances, and/or motor abnormalities). Studies conducted between 1941 and 1958 at Walter Reed Medical Center show that about 10% of febrile diseases with central nervous system involvement were due to LCMV (1, 5). While meningitis and encephalitis patients require hospitalization and supportive care based on severity of symptoms, infected individuals usually recover fully without sequelae, although nerve deafness and arthritis have been reported. Mortality resulting from LCMV infection is rare, occurring in less than 1% of cases (11).

LCMV can be transmitted from an infected pregnant woman to the developing fetus resulting in severe teratogenic consequences including hydrocephaly, microcephaly or macrocephaly, and chorioretinitis (14). These conditions commonly lead to severe developmental delays, mental retardation, blindness, and premature death. The incidence of congenital LCMV infection among infants born in the US has not been established (14).

Recently, new manifestations of LCMV-associated diseases have been reported in the medical literature (3). In 2002 and again in 2005, LCMV was transmitted to patients receiving immunosuppressive medications after they received transplanted organs from an infected donor. Out of eight organ recipients, seven died from the infection. The donors exhibited no clinical signs of LCMV infection and subsequent diagnostic investigations failed to detect the virus. Nevertheless, the coincidence in timing and phylogenetic matching of strains within each cluster provide convincing evidence regarding the origins of the infecting agents (3).

Prevention and treatment options for LCMV are limited. No licensed vaccines or FDA-approved antiviral drugs are available. Although ribavirin has shown limited antiviral activity against LCMV in vitro, there exists no established data supporting its routine use in humans. Thus there remains a need to develop safe and effective products to protect against LCMV infections.

The arenavirus genome consists of two segments of single-stranded RNA, each of which codes for two genes in opposite orientations (referred to as ambisense). The larger of the two segments, the L RNA (7.2 kb), encodes the L and Z proteins. The L protein is the RNA-dependent RNA polymerase (RdRp), and the Z protein is a small zinc-binding RING finger protein which is involved in virus budding (10). The S RNA (3.4 kb) encodes the nucleoprotein (NP) and the envelope glycoprotein precursor (GP-C). The nucleocapsid consists of genomic RNA tightly encapsidated by viral NP, the most abundant viral protein in virions and infected cells.

The L protein is a circa 254 kDa multifunctional enzyme that possesses characteristics shared with over 80 RdRps from negative-strand viruses, including six conserved domains that appear to correspond to essential functional features required to synthesize RNA from RNA template (13). Viral RNA, NP, and L combine to form a ribonucleoprotein complex, which transcribes and replicates the viral genome (4). Because mammalian cells lack homologs of the L and NP proteins, the potential to specifically inhibit these enzymes without compromising essential host processes make NP and L attractive targets for antiviral therapeutic development efforts.

SUMMARY OF THE INVENTION

The present invention provides a pharmaceutical composition comprising a pharmaceutically acceptable carrier and a compound having the following general Formula I or a pharmaceutically acceptable salt thereof:

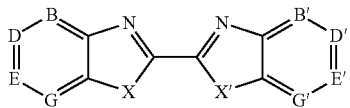

Formula I wherein B, D, E, G, B', D', E' and G' are independently N or C—R;

R is selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, alkylsulfonyl, arylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro; and X and X' are independently selected from the group consisting of O, S or N—R', wherein R' is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl and substituted carbamoyl.

The present invention also provides a compound having the following general Formula I or a pharmaceutically acceptable salt thereof:

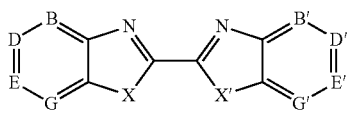

Formula I wherein B, D, E, G, B', D', E' and G' are independently N or C—R;

R is selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, alkylsulfonyl, arylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro; with a proviso that at least one of B, D, E, G, B', D', E' and G' is C—Y, wherein Y is halogen, and
   (i) if none of B, E, G, B', E' and G' is N, D and D' are not both C—F or C—Cl;
   (ii) if none of D, E, G, D', E' and G' is N, B and B' are not both C—Br; or
   (iii) if none of B, E, G, B', E' and G' is N and when D is C—Br, D' is not C—Z, wherein Z is 4-methyl-1-piperazinyl; and X and X' are independently selected from the group consisting of O, S or N—R', wherein R' is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl and substituted carbamoyl.

The present invention further provides a compound or a pharmaceutically acceptable salt thereof selected from the group consisting of 4,4'-Dimethoxy-1H,1'H-[2,2']bibenzoimidazolyl; 1H,1'H-[2,2']Bibenzoimidazolyl-4,4'-dicarboxylic acid dimethyl ester; 1H,1'H-[2,2']Bibenzoimidazolyl-5,5'-dicarboxylic acid dimethyl ester; and 4,4'-Diphenyl-1H,1'H-[2,2']bibenzoimidazolyl.

The present invention also provides a method for the treatment or prophylaxis of a viral infection or disease associated therewith, comprising administering in a therapeutically effective amount to a mammal in need thereof, a compound of Formula I below or a pharmaceutically acceptable salt thereof:

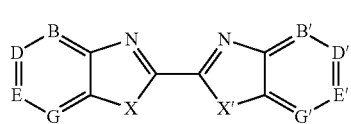

Formula I wherein B, D, E, G, B', D', E' and G' are independently N or C—R;

R is selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, alkylsulfonyl, arylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro; and X and X' are independently selected from the group consisting of O, S or N—R', wherein R' is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl and substituted carbamoyl.

Other objects and advantages of the present invention will become apparent from the following description and appended claims.

DETAILED DESCRIPTION OF THE INVENTION

The compounds of the invention are of the following general Formula I:

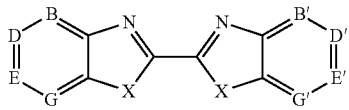

Formula I wherein B, D, E, G, B', D', E' and G' are independently N or C—R;

R is selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, alkylsulfonyl, arylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro; and X and X' are independently selected from the group consisting of O, S or N—R', wherein R' is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl and substituted carbamoyl.

Preferably each of B, D, E, G, B', D', E' and G' is C—R. Also preferably, R is selected from the group consisting of hydrogen, alkyl, amino and halogen. More preferably, R is hydrogen or methyl.

Preferably, each of X and X' is N—R' wherein R' is hydrogen or alkyl.

Preferably, the compound of the present invention is selected from the group consisting of 1H,1'H-[2,2']Bibenzoimidazolyl; 5,6,5',6'-Tetramethyl-1H,1'H-[2,2']bibenzoimidazolyl; 1,1'-Dimethyl-1H,1'H-[2,2']bibenzoimidazolyl; 1,1'-Diethyl-1H,1'H-[2,2']bibenzoimidazolyl; 6,6'-Dinitro-1H,1'H-[2,2']bibenzoimidazolyl; 4,4'-Difluoro-1H,1'H-[2,2']bibenzoimidazolyl; 5,5'-Difluoro-1H,1'H-[2,2']bibenzoimidazolyl; 5,5'-Dichloro-1H,1'H-[2,2']bibenzoimidazolyl; 5,5'-Dibromo-1H,1'H-[2,2']bibenzoimidazolyl; 4,4'-Dimethyl-1H,1'H-[2,2']bibenzoimidazolyl; 5,5'-Dimethyl-1H,1'H-[2,2']bibenzoimidazolyl; 4,4'-Dimethoxy-1H,1'H-[2,2']bibenzoimidazolyl; 5,5'-Dimethoxy-1H,1'H-[2,2']bibenzoimidazolyl; 1H,1'H-[2,2']Bibenzoimidazolyl-4,4'-dicarboxylic acid dimethyl ester; 1H,1'H-[2,2']Bibenzoimidazolyl-5,5'-dicarboxylic acid dimethyl ester; 4,4'-Diphenyl-1H,1'H-[2,2']bibenzoimidazolyl; 4,5,4',5'-Tetrafluoro-1H,1'H-[2,2']bibenzoimidazolyl; 4,6,4',6'-Tetrafluoro-1H,1'H-[2,2']bibenzoimidazolyl; 5,6,5',6'-Tetrafluoro-1H,1'H-[2,2']bibenzoimidazolyl; 1H,1'H-[2,2']Bi[imidazo[4,5-b]pyridinyl]; 3H,3'H-[2,2']Bi[imidazo[4,5-c]pyridinyl]; 4,7,4',7'-Tetrafluoro-1H,1'H-[2,2']bibenzoimidazolyl; and 4,4'-Dichloro-1H,1'H-[2,2']bibenzoimidazolyl.

More preferably, the compound of Formula I is 1H,1'H-[2,2']Bibenzoimidazolyl; 4,4'-Difluoro-1H,1'H-[2,2']bibenzoimidazolyl; 5,5'-Difluoro-1H,1'H-[2,2']bibenzoimidazolyl; or 4,6,4',6'-Tetrafluoro-1H,1'H-[2,2']bibenzoimidazolyl.

The method of the present invention is for the treatment or prophylaxis of a viral infection or disease associated therewith, comprising administering in a therapeutically effective amount to a mammal in need thereof, a compound of Formula I described above.

Preferably, the mammal is a human and the viral infection is an arenavirus infection. More preferably, the arenavirus virus is selected from the group consisting of Lassa, Junín, Machupo, Guanarito, Sabia, Whitewater Arroyo, Chapare, LCMV, LCMV-like viruses such as Dandenong, Tacaribe, and Pichinde.

Preferably, the viral infection is associated with a condition selected from the group consisting of viral hemorrhagic fever, meningitis, meningoencephalitis, encephalitis, or arenavirus-mediated disease in organ transplant recipients. Additionally, the patient could be a pregnant patient with a risk of congenital or perinatal transmission of LCMV, in which the desired outcome is the prevention or reduction of LCMV-associated pathologies such as infant mortality, microcephaly, mental retardation, chorioretinitis, and hydrocephalus.

The method of the present invention may also comprise co-administration of: a) other antivirals such as ribavirin or cidofovir; b) vaccines; and/or c) interferons or pegylated interferons.

Definitions

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, experimental animals including rats, mice, and guinea pigs, domestic and farm animals, and zoo, sports, or pet animals, such as dogs, horses, cats, cows, and the like.

The term "efficacy" as used herein refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkylamino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Amino" refers to the group —NH$_2$.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one, and the like) provided that the point of attachment is through an aromatic ring atom.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OS(O)$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substiruted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substiruted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Halo" or "halogen" refers to fluoro, chloro, bromo and iodo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (=O). The term "heteroaryl having two nitrogen atoms in the heteroaryl, ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$ -cycloalkyl, —S(O)$_2$-substituted cycloalkyl, —S(O)$_2$ -alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substiruted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Sulfonyl" refers to the group —S(O)$_2$R where R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable. Pharmaceutically-acceptable salts refer to pharmaceutically-acceptable salts of the compounds, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Pro-drugs are prepared by modifying functional groups present in such a way that the modifications may be cleaved in vivo to release the parent compound. Pro-drugs include compounds wherein a hydroxy, amino, or sulfhydryl group is bonded to any group that may be cleaved in vivo to regenerate the free hydroxyl, amino, or sulfhydryl group, respectively. Examples of pro-drugs include, but are not limited to esters (e.g., acetate, formate, and benzoate derivatives), carbamates (e.g., N,N-dimethylamino-carbonyl) of hydroxy functional groups, and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically-effective amount" means the amount of a compound that, when administered to a mammal for treating a disease, is sufficient to effect such treatment for the disease. The "therapeutically-effective amount" will vary depending on the compound, the disease, and its severity and the age, weight, etc., of the mammal to be treated.

Synthesis of Compounds

The compounds are readily prepared via several divergent synthetic routes with the particular route selected relative to the ease of compound preparation, the commercial availability of starting materials, and the like.

The compounds can be prepared from readily-available starting materials using the following general methods and procedures. It will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included unless otherwise indicated. Pure stereoisomers (or enriched mixtures) may be prepared using, for example, optically-active starting materials or stereoselective reagents well-known in the art. Alternatively, racemic mixtures of such compounds can be separated using, for example, chiral column chromatography, chiral resolving agents, and the like.

Unless otherwise indicated, if the products contain chiral centers, they are a mixture of R, S enantiomers. However, when a chiral product is desired, the chiral product can be obtained via purification techniques which separate enantiomers from a R, S mixture to provide for one or the other stereoisomer. Such techniques are known in the art.

The compounds can be provided as pro-drugs which convert (e.g., hydrolyze, metabolize, etc.) in vivo to a compound above.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of 24 pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate Particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by, route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug.

Generally, the amount of buffer used is able to maintain a formulation pH in the range of 4 to 8. Generally, a 1:1 to 10:1 mole ratio of buffer (where the moles of buffer are taken as the combined moles of the buffer ingredients, e.g., sodium citrate and citric acid) to drug is used.

A useful buffer is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the compounds, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or polyvinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host.

Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

The provided compounds and pharmaceutical compositions show biological activity in treating and preventing viral infections and associated diseases, and, accordingly, have utility in treating viral infections and associated diseases, such as LCMV and hemorrhagic fever viruses, in mammals including humans.

Hemorrhagic fever viruses (HFVs) are RNA viruses that cause a variety of disease syndromes with similar clinical characteristics. HFVs that are of concern as potential biological weapons include but are not limited to: Arenaviridae (Junin, Machupo, Guanarito, Sabia, and Lassa), Filoviridae (Ebola and Marburg viruses), Flaviviridae (yellow fever, Omsk hemorrhagic fever and Kyasanur Forest disease viruses), and Bunyaviridae (Rift Valley fever and Crimean-Congo hemorrhagic fever). The naturally-occurring arenaviruses and potential engineered arenaviruses are included in the Category A Pathogen list according to the Centers for Disease Control and Prevention as being among those agents that have greatest potential for mass casualties.

Risk factors include: travel to Africa or Asia, handling of animal carcasses, contact with infected animals or people, and/or arthropod bites. Arenaviruses are highly infectious after direct contact with infected blood and/or bodily secretions. Humans usually become infected through contact with infected rodents, the bite of an infected arthropod, direct contact with animal carcasses, inhalation of infectious rodent excreta and/or injection of food contaminated with rodent excreta. The Tacaribe virus has been associated with bats. Airborne transmission of hemorrhagic fever is another mode. Person-to-person contact may also occur in some cases. LCMV is prevalent world-wide and associated with the common house mouse Mus musculus, as well as certain other rodents such as hamsters and guinea pigs. Risk factors include proximity to mouse habitats or excreta, or exposure to pet rodents.

All of the hemorrhagic fevers exhibit similar clinical symptoms. However, in general the clinical manifestations are non-specific and variable. The incubation period is approximately 7-14 days. The onset is gradual with fever and malaise, tachypnea, relative bradycardia, hypotension, circulatory shock, conjunctival infection, pharyngitis, lymphadenopathy, encephalitis, myalgia, back pain, headache and dizziness, as well as hyperesthesia of the skin. Some infected patients may not develop hemorrhagic manifestations.

Methods of diagnosis at specialized laboratories include antigen detection by antigen-capture enzyme-linked immunosorbent assay (ELISA), IgM antibody detection by antibody-capture enzyme-linked immunosorbent assay, reverse transcriptase polymerase chain reaction (RT-PCR), and viral isolation. Antigen detection (by enzyme-linked immunosorbent assay) and reverse transcriptase polymerase chain reaction are the most useful diagnostic techniques in the acute clinical setting.

In the examples below, if an abbreviation is not defined above, it has its generally accepted meaning. Further, all temperatures are in degrees Celsius (unless otherwise indicated). The following Methods were used to prepare the compounds set forth below as indicated.

EXAMPLE 1

General Synthetic Procedure

The bibenzimidazoles of this invention were obtained from commercial sources or prepared following the procedures described in *J. Chem. Soc., Perkin Trans. I*, 1967, 1, 20-25 and *Inorg. Chem.* 1978, 17, 2078-2083. The procedures are summarized in the following synthetic scheme.

Two equivalents of diamine reacting with one equivalent of methyl 2,2,2-trichloroacetimidate or oximide yield the desired product. The products can usually be isolated by precipitation into water, followed by recrystallization or trituration with different solvents. The products are then characterized with NMR, Mass spectroscopy and/or melting point determination. The analytical data are summarized in Table 1 below.

EXAMPLE 2

Formulation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

EXAMPLE 3

Formulation 2

A tablet formula is prepared using the ingredients below:

| Ingredient | Quantity (mg/capsule) |
|---|---|
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

EXAMPLE 4

Formulation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

EXAMPLE 5

Formulation 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

EXAMPLE 6

Formulation 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

EXAMPLE 7

Formulation 6

Suppositories, each containing 25 mg of active ingredient, are made as follows:

| Ingredient | Amount |
|---|---|
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 8

Formulation 7

Suspensions, each containing 50 mg of medicament per 5.0 ml dose, are made as follows:

| Ingredient | Amount |
| --- | --- |
| Active Ingredient | 50.0 mg |
| Xanthan gum | 4.0 mg |
| Sodium carboxymethyl cellose (11%) | |
| Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a NO. 1 0 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 9

Formulation 8

Hard gelatin tablets, each containing 15 mg of active ingredient, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

EXAMPLE 10

Formulation 9

An intravenous formulation may be prepared as follows:

| Ingredient | (mg/capsule) |
| --- | --- |
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

EXAMPLE 11

Formulation 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

EXAMPLE 12

Formulation 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final Concentration |
| --- | --- | --- |
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/100.0 mL | Final Concentration |
| --- | --- | --- |
| Candidate Compound | 0.300 g | 30.0 mg/mL |
| .05% Sodium Bicarbonte/Saline Stock Solution | q.s. ad 10.0 mL | q.s. ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.

4. Q.S. to 10.0 mL with 0.5% sodium bicarbonate/saline stock solution and mix.

EXAMPLE 13

Determining Antiviral Activity of Compounds of the Invention

Because LCMV forms noncytolytic infections (9), a cell-based Enzyme-Linked ImmunoSorbent Assay (ELISA) was employed to screen a small-molecule compound library for antiviral activity using the Armstrong strain of LCMV (Arm53b). Briefly, Vero cell monolayers were infected at a low multiplicity of infection in the presence of test compounds at a concentration of 5 μM. After a 5-day incubation period, a monoclonal antibody was used to detect viral NP within infected cells. The cell-based nature of this assay, using authentic infectious LCMV, permitted detection of compounds capable of inhibiting any process required for viral replication. Compound 1 (see Table 1 below) was identified as a hit from this screening and was further investigated for tractability, potency, and selectivity.

A chemically tractable compound is defined as one that is synthetically accessible using reasonable chemical methodology, and which possesses chemically stable functionalities and potential drug-like qualities. Compound 1 passed this medicinal chemistry filter and was evaluated for potency. Compound potency was determined by evaluating inhibitory activity across a broad range of concentrations, again using the cell-based ELISA. Nonlinear regression was used to generate best-fit inhibition curves and to calculate a 50% effective concentration ($EC_{50}$) equivalent to 80 nM. The selectivity or specificity of a given compound is typically expressed as a ratio of its cytotoxicity to its biological effect. A cell proliferation assay is used to calculate a 50% cytotoxicity concentration ($CC_{50}$); the ratio of this value to the $EC_{50}$ is referred to as the therapeutic index (T.I.=$CC_{50}/EC_{50}$). To determine cytotoxicity, a fluorimetric assay that quantifies reduction of resazurin (Alamar Blue) was employed (8). Compound 1 exhibited no quantifiable cytotoxic effects at concentrations up to 25 μM, making the T.I. for this compound >310.

Broad evaluation of the mechanism of action for Compound 1 was performed. In LCMV-infected cells in the presence of 10 μM compound, synthesis of viral S RNA and NP mRNA were dramatically suppressed relative to untreated controls for a period of at least 48 h post infection. Replication and transcription of viral RNA was also evaluated by monitoring the activity of a reporter gene, chloramphenicol acetyltransferase (CAT), encoded in a negative-sense orientation on an RNA analog, the design of which is based on the essential replicative elements of LCMV genomic RNA (4). In this cell-based assay, replication and transcription of the artificial RNA analog is facilitated by plasmid-encoded viral. NP and L proteins. No CAT activity was observed in infected cells treated with 20 μM of Compound 1. Taken together, these results suggest that Compound 1 inhibits the activity of either viral NP or L protein, preventing efficient transcription and translation of viral RNA.

Chemical analogs of this compound were obtained from commercial vendors or were synthesized, and these analogs were tested as described in order above to define the relationship between chemical structure and biological activity. Several analogs were tested for antiviral activities as shown in Table 1 below. Two analogs, Compounds 6 and 7, displayed enhanced potency ($EC_{50}$=6 nM and 63 nM, respectively) and selectivity relative to Compound 1.

TABLE 1

The anti-viral activity of compounds of the present invention.

Activity
A: $EC_{50} < 1$ uM;
B: $1 < EC_{50} < 10$ uM;
C: $10 < EC_{50} < 25$ uM;
D: $EC_{50} > 25$ uM; n.d.: not determined

| Compound | Chemical Structure | Molecular Formula | Analytical Data | Chemical Name | Activity |
|---|---|---|---|---|---|
| 1 | 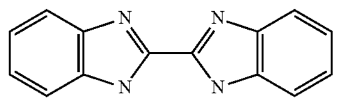 [SMILES: c1ccc2[nH]c(-c3nc4ccccc4[nH]3)nc2c1] | C14 H10 N4 | $^1$H NMR in DMSO-d6: δ 13.55 (s, 2H), 7.76 (d, 2H), 7.56 (d, 2H), 7.29 (td, 4H); $^{13}$C NMR in DMSO-d6: δ 143.81, 143.49, 134.83, 123.63, 122.25, 119.18, 112.06; HRMS: 234.08976 M$^+$ | 1H,1'H-[2,2']Bibenzoimidazolyl | A |
| 2 | 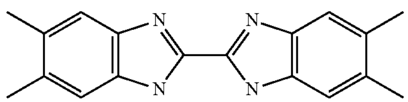 | C18 H18 N4 | | 5,6,6',6'-Tetramethyl-1H,1'H-[2,2']bibenzoimidazolyl | B |
| 3 | 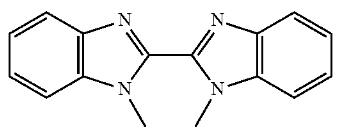 [SMILES: Cn1c(-c2nc3ccccc3n2C)nc2ccccc21] | C16 H14 N4 | | 1,1'-Dimethyl-1H,1'H-[2,2']bibenzoimidazolyl | D |
| 4 | 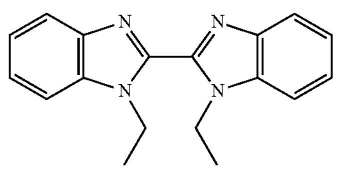 [SMILES: CCn1c(-c2nc3ccccc3n2CC)nc2ccccc21] | C18 H18 N4 | | 1,1'-Dimethyl-1H,1'H-[2,2']bibenzoimidazolyl | D |
| 5 | 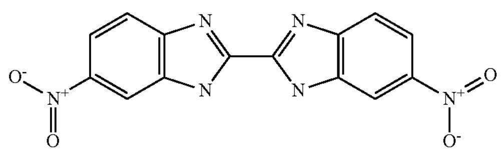 [SMILES: O=[N+]([O-])c1ccc2nc(-c3nc4ccc([N+](=O)[O-])cc4[nH]3)[nH]c2c1] | C14 H8 N6 O4 | | 6,6'-Dinitro-1H,1'H-[2,2']bibenzoimidazolyl | D |
| 6 | 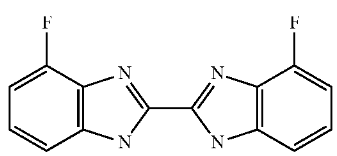 | C14 H8 F2 N4 | $^1$H NMR in DMSO-d6: δ 14.04 (br s, 2H), 12.02 (br s, 1H), 7.26-7.45 (m, 4H), 7.07-7.17 (m, 2H); Mass Spec: 269.3 (M – H) | 4,4'-Difluoro-1H,1'H-[2,2']bibenzoimidazolyl | A |

TABLE 1-continued

The anti-viral activity of compounds of the present invention.

| Compound | Chemical Structure | Molecular Formula | Analytical Data | Chemical Name | Activity A: EC$_{50}$ < 1 uM; B: 1 < EC$_{50}$ < 10 uM; C: 10 < EC$_{50}$ < 25 uM; D: EC$_{50}$ > 25 uM; n.d.: not determined |
|---|---|---|---|---|---|
| 7 | 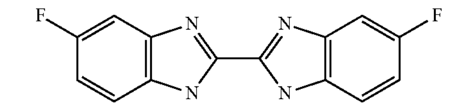 [SMILES: Fc1ccc2[nH]c(-c3nc4cc(F)ccc4[nH]3)nc2c1] | C14 H8 F2 N4 | $^1$H NMR in DMSO-d6: δ 7.76-7.82 (m, 1H), 7.54-7.68 (m, 2H), 7.12-7.34 (m, 3H); Mass Spec: 269.3 (M − H)$^-$ | 5,5'-Difluoro-1H,1'H-[2,2']bibenzoimidazolyl | A |
| 8 | 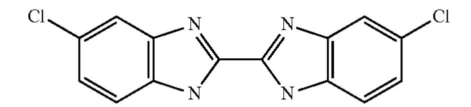 [SMILES: Clc1ccc2[nH]c(-c3nc4cc(Cl)ccc4[nH]3)nc2c1] | C14 H8 Cl2 N4 | $^1$H NMR in DMSO-d6: δ 7.71 (s, 2H), 7.67 (s, 2H), 7.35 (dd, 2H); Mass Spec: 301.2 (M − H)$^-$ | 5,5'-Dichloro-1H,1'H-[2,2']bibenzoimidazolyl | B |
| 9 | 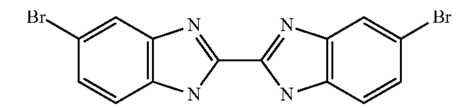 [SMILES: Brc1ccc2[nH]c(-c3nc4cc(Br)ccc4[nH]3)nc2c1] | C14 H8 Br2 N4 | $^1$H NMR in DMSO-d6: δ 7.86 (s, 2H), 7.64 (d, 2H), 7.47 (dd, 2H); Mass Spec: 391.1 (M − H)$^-$ | 5,5'-Dibromo-1H,1'H-[2,2']bibenzoimidazolyl | B |
| 10 | 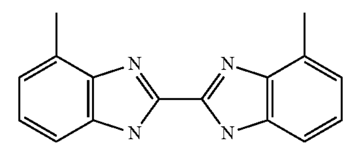 | C16 H14 N4 | $^1$H NMR in DMSO-d6: δ 7.50 (d, 2H), 7.22 (t, 2H), 7.11 (d, 2H), 2.66 (s, 6H); Mass Spec: 363.2 (M + H)$^+$ | 4,4'-Dimethyl-1H,1'H-[2,2']bibenzoimidazolyl | D |
| 11 | 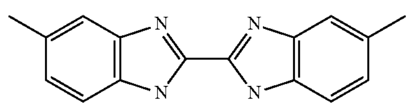 | C16 H14 N4 | $^1$H NMR in DMSO-d6: δ 13.38 (br s, 1H), 12.00 (br s, 1H), 7.63 (d, 1H), 7.55 (s, 1H), 7.44 (d, 1H), 7.35 (s, 1H), 7.12 (t, 2H), 2.47 (s, 6H); Mass Spec: 363.3 (M + H)$^+$; 361.3 (M − H)$^-$ | 5,5'-Dimethyl-1H,1'H-[2,2']bibenzoimidazolyl | D |
| 12 | 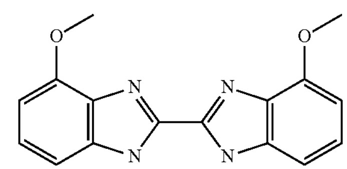 [SMILES: COc1cccc2[nH]c(-c3nc4c(OC)cccc4[nH]3)nc12] | C16 H14 N4 O2 | $^1$H NMR in DMSO-d6: δ 7.21-7.36 (m, 4H), 6.89 (d, 2H), 4.01 (s, 6H); Mass Spec: 295.2 (M + H)$^+$ | 4,4'-Dimethoxy-1H,1'H-[2,2']bibenzoimidazolyl | D |
| 13 | 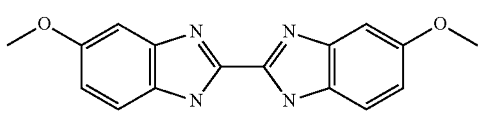 | C16 H14 N4 O2 | $^1$H NMR in DMSO-d6: δ 7.57 (d, 2H), 7.08 (s, 2H), 6.92 (dd, 2H), 3.84 (s, 6H); Mass Spec: 295.2 (M + H)$^+$ | 5,5'-Dimethoxy-1H,1'H-[2,2']bibenzoimidazolyl | C |

TABLE 1-continued

The anti-viral activity of compounds of the present invention.

| Compound | Chemical Structure | Molecular Formula | Analytical Data | Chemical Name | Activity<br>A: $EC_{50} < 1$ uM;<br>B: $1 < EC_{50} < 10$ uM;<br>C: $10 < EC_{50} < 25$ uM;<br>D: $EC_{50} > 25$ uM; n.d.: not determined |
|---|---|---|---|---|---|
| 14 | 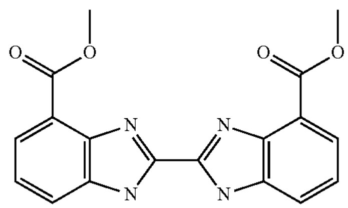 [SMILES: COC(=O)c1cccc2[nH]c(-c3nc4c(C(=O)OC)cccc4[nH]3)nc12] | C18 H14 N4 O4 | $^1$H NMR in DMSO-d6: δ 8.13 (d, 2H), 7.99 (d, 2H), 7.47 (t, 2H), 4.05 (s, 6H); Mass Spec: 351.0 (M + H)$^+$; 373.1 (M + Na)$^+$ | 1H,1'H-[2,2']Bibenzoimidazolyl-4,4'-dicarboxylic acid dimethyl ester | D |
| 15 | 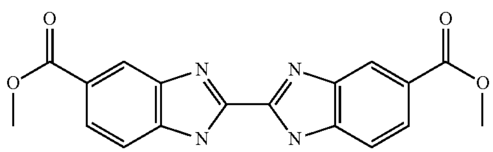 [SMILES: COC(=O)c1ccc2[nH]c(-c3nc4cc(C(=O)OC)ccc4[nH]3)nc2c1] | C18 H14 N4 O4 | $^1$H NMR in DMSO-d6: δ 14.10 (br s, 1H), 11.99 (br s, 1H), 8.38 (s, 1H), 8.22 (s, 1H), 7.96 (m, 3H), 7.71 (d, 1H), 3.93 (s, 6H): Mass Spec: 349.3 (M − H)$^-$ | 1H,1'H-[2,2']Bibenzoimidazolyl-5,5'-dicarboxylic acid dimethyl ester | D |
| 16 | 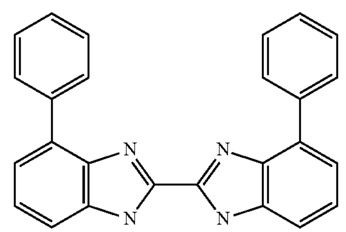 [SMILES: c1ccc(-c2cccc3[nH]c(-c4nc5c(-c6ccccc6)cccc5[nH]4)nc23)cc1] | C26 H18 N4 | $^1$H NMR in DMSO-d6: δ 8.04 (d, 4H), 7.38-7.64 (m, 12H); Melting point (uncorrected): 247-250° C. (decompose) | 4,4'-Diphenyl-1H,1'H-[2,2']bibenzoimidazolyl | D |
| 17 | 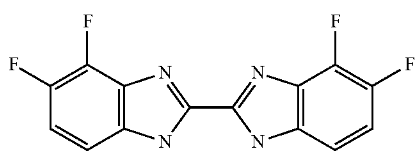 [SMILES: Fc1ccc2[nH]c(-c3nc4c(F)c(F)ccc4[nH]3)nc2c1F] | C14 H6 F4 N4 | $^1$H NMR in DMSO-d6: δ 7.37-7.44 (m, 4H) | 4,5,4',5'-Tetrafluoro-1H,1'H-[2,2']bibenzoimidazolyl | A |
| 18 | 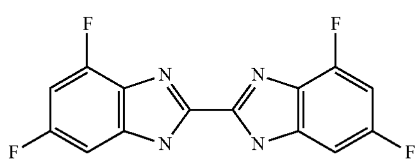 [SMILES: Fc1cc(F)c2nc(-c3nc4c(F)cc(F)cc4[nH]3)[nH]c2c1] | C14 H6 F4 N4 | $^1$H NMR in DMSO-d6: δ 14.17 (s, 1H), 12.00 (s, 1H), 7.13-7.26 (m, 4H) | 4,6,4',6'-Tetrafluoro-1H,1'H-[2,2']bibenzoimidazolyl | A |

TABLE 1-continued

The anti-viral activity of compounds of the present invention.

| Compound | Chemical Structure | Molecular Formula | Analytical Data | Chemical Name | Activity<br>A: EC$_{50}$ < 1 uM;<br>B: 1 < EC$_{50}$ < 10 uM;<br>C: 10 < EC$_{50}$ < 25 uM;<br>D: EC$_{50}$ > 25 uM; n.d.: not determined |
|---|---|---|---|---|---|
| 19 | 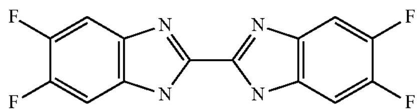 | C14 H6 F4 N4 | $^1$H NMR in DMSO-d6: δ 7.48 (t, 4H); Mass Spec: 305.4 (M − H)$^−$ | 5,6,5',6'-Tetrafluoro-1H,1'H-[2,2']bibenzoimidazolyl | A |
| 20 | 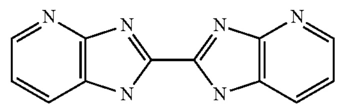 [SMILES: c1cnc2nc(-c3nc4ncccc4[nH]3)[nH]c2c1] | C12 H8 N6 | | 1H,1'H-[2,2']Bi[imidazo[4,5 b]pyridinyl] | A |
| 21 | 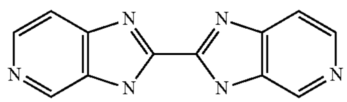 [SMILES: c1cc2nc(-c3nc4ccncc4[nH]3)[nH]c2cn1] | C12 H8 N6 | Mass Spec: 237.3 (M + H)$^+$; Melting point (uncorrected): >300° C. | 3H,3'H-[2,2']Bi[imidazo[4,5 c]pyridinyl] | C |
| 22 | 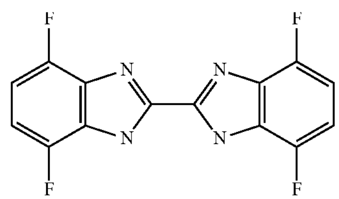 [SMILES: Fc1ccc(F)c2[nH]c(-c3nc4c(F)ccc(F)c4[nH]3)nc12] | C14 H6 F4 N4 | | 4,7,4',7'-Tetrafluoro-1H,1'H-[2,2']bibenzoimidazolyl | n.d. |
| 23 | 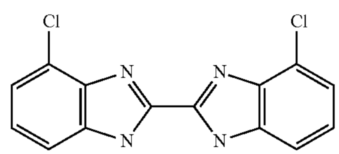 [SMILES: Clc1cccc2[nH]c(-c3nc4c(Cl)cccc4[nH]3)nc12] | C14 H8 Cl2 N4 | | 4,4'-Dichloro-1H,1'H-[2,2']bibenzoimidazolyl | n.d. |

REFERENCES

1. Adair, C. V., R. L. Gauld, and J. E. Smadel. 1953. Aseptic meningitis, a disease of diverse etiology: clinical and etiologic studies on 854 cases. Ann. Intern. Med. 39:675-704.
2. Buchmeier, M. J., M. D. Bowen, and C. J. Peters. 2001. Arenaviridae: the viruses and their replication, p. 1635-1668. In D. M. Knipe and P. M. Howley (ed.), Fields Virology, 4th ed. Lippincott, Williams and Wilkins, Philadelphia Pa.
3. Fischer, S. A., M. B. Graham, M. J. Kuehnert, C. N. Kotton, A. Srinivasan, F. M. Marty, J. A. Corner, J. Guarner, C. D. Paddock, D. L. DeMeo, W. -J. Shieh, B. R. Erickson, U. Bandy, A. DeMaria, Jr., J. P. Davis, F. L. Delmonico, B. Pavlin, A. Likos, M. J. Vincent, T. K. Sealy, C. S. Goldsmith, D. B. Jernigan, P. E. Rollin, M. M. Packard, M. Patel, C. Rowland, R. F. Helfand, S. T. Nichol, J. A. Fishman, T. Ksiazek, S. R. Zaki, and the LCMV in Transplant Recipients Investigation Team. 2006. Transmission of lymphocytic choriomeningitis virus by organ transplantation. N. Engl. J. Med. 354:2235-2249.
4. Lee, K. J., I. S, Novella, M. N. Teng, M. B. A. Oldstone, and J. C. de la Torre. 2000. NP and L proteins of lymphocytic choriomeningitis virus (LCMV) are sufficient for efficient transcription and replication of LCMV genomic RNA analogs. J. Virol. 74:3470-3477.
5. Meyer, H. M., Jr., R. T. Johnson, I. P. Crawford, H. E. Dascomb, and N. G. Rogers. 1960. Central nervous system syndromes of "vital" etiology. A study of 713 cases. Am. J. Med. 29:334-347.
6. NIAID. 2002. NIAID biodefense research agenda for CDC category A agents. NIH Publication No. 03-5308.
7. NIAID. 2007. NIAID category A, B and C priority pathogens. http://www3.niaid.nih.gov/biodefense/PDF/cat.pdf, accessed Dec. 6, 2007.
8. O'Brien, J., I. Wilson, T. Orton, and F. Pognan. 2000. Investigation of the Alamar Blue (resazurin) fluorescent dye for the assessment of mammalian cell cytotoxicity. Eur. J. Biochem. 267:5421-5426.
9. Oldstone, M. B. A. 2007. A suspenseful game of 'hide and seek' between virus and host. Nat. Immunol. 8:325-327.
10. Perez, M., R. C. Craven, and J. C. de la Torre. 2003. The small RING finger protein Z drives arenavirus budding: implications for antiviral strategies. Proc. Natl. Acad. Sci. USA 100:12978-12983.
11. Peters, C. J. 2006. Lymphocytic choriomeningitis virus—an old enemy up to new tricks. N. Engl. J. Med. 354:2208-2211.
12. Rotz, L. D., A. S. Khan, S. R. Lillibridge, S. M. Ostroff, and J. M. Hughes. 2002. Public health assessment of potential biological terrorism agents. Emerg. Infect. Dis. 8:225-230.
13. Sánchez, A. B., and J. C. de la Torre. 2005. Genetic and biochemical evidence for an oligomeric structure of the functional L polymerase of the prototypic arenavirus lymphocytic choriomeningitis virus. J. Virol. 79:7262-7268.
14. Wright, R., D. Johnson, M. Neumann, T. G. Ksiazek, P. Rollin, R. V. Keech, D. J. Bonthius, P. Hitchon, C. F. Grose, W. E. Bell, and J. F. Bale, Jr. 1997. Congenital lymphocytic choriomeningitis virus syndrome: a disease that mimics congenital toxoplasmosis or cytomegalovirus infection. Pediatrics 100:e9.

All references cited herein are herein incorporated by reference in their entirety for all purposes.

The invention has been described in terms of preferred embodiments thereof, but is more broadly applicable as will be understood by those skilled in the art. The scope of the invention is only limited by the following claims.

What is claimed is:

1. A method of inhibiting or causing regression of an Arenavirus infection, comprising administering in a therapeutically effective amount to a mammal in need thereof, a compound of Formula I below or a pharmaceutically acceptable salt thereof:

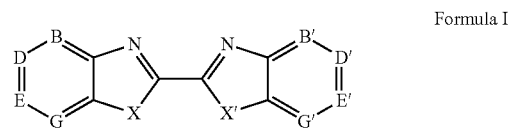

Formula I wherein each of B, D, E, G, B', D', E' and G' is C—R and;
R is selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, alkylsulfonyl, arylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro; and
wherein each of X and X' is N—R' and R' is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl and substituted carbamoyl.

2. The method of claim 1, wherein that at least one of B, D, E, G, B', D', E' and G' is C—Y, wherein Y is halogen.

3. The method of claim 1, wherein R is selected from the group consisting of hydrogen, alkyl, amino and halogen.

4. The method of claim 3, wherein, R is hydrogen or methyl.

5. The method of claim 1, wherein R' is hydrogen or alkyl.

6. The method of claim 1, wherein the compound of Formula I is selected from the group consisting of 1H,1'H-[2,2']Bibenzoimidazolyl; 5,6,5',6'-Tetramethyl-1H, 1'H-[2,2']bibenzoimidazolyl; 1,1'-Dimethyl-1H, 1'H-[2,2']bibenzoimidazolyl; 1,1'-Diethyl-1H, 1'H-[2,2']bibenzoimidazolyl; 6,6'-Dinitro-1H,1'H-[2,2']bibenzoimidazolyl; 4,4'-Difluoro-1H,1'H-[2,2']bibenzoimidazolyl; 5,5'-Difluoro-1H,1'H-[2,2']bibenzoimidazolyl; 5,5'-Dichloro-1H,1'H-[2,2']bibenzoimidazolyl; 5,5'-Dibromo-1H,1'H-[2,2']bibenzoimidazolyl; 4,4'-Dimethyl-1H,1'H-[2,2']bibenzoimidazolyl; 5,5'-Dimethyl- 1H,1'H-[2,2']bibenzoimidazolyl; 4,4'-Dimethoxy-1H,1'H[2,2']bibenzoimidazolyl; 5,5'-Dimethoxy-1H,1'H[2,2']bibenzoimidazolyl;
1H,1'H-[2,2']Bibenzoimidazolyl-4,4'-dicarboxylic acid dimethyl ester; 1H,1'H-[2,2']Bibenzoimidazolyl-5,5'-dicarboxylic acid dimethyl ester; 4,4'-Diphenyl-1H,1'H-[2,2']bibenzoimidazolyl; 4,5,4',5'-Tetrafluoro-1H,1'H-[2,2']bibenzoimidazolyl; 4,6,4',6'-Tetrafluoro-1H,1'H-

[2,2']bibenzoimidazolyl; 5,6,5',6'-Tetrafluoro-1H,1'H-[2,2']bibenzoimidazolyl; 4,7,4',7'-Tetrafluoro-1H,1'H-[2,2']bibenzoimidazolyl; and 4,4'-Dichloro-1H,1'H-[2,2']bibenzoimidazolyl.

7. The method of claim 1, wherein the compound of Formula I is selected from the group consisting 1H,1'H-[2,2']Bibenzoimidazolyl; 4,4'-Difluoro-1H,1'H-[2,2']bibenzoimidazolyl; 5,5'-Difluoro-1H,1'H-[2,2']bibenzoimidazolyl; and 4,6,4',6'-Tetrafluoro-1H,1'H-[2,2']bibenzoimidazolyl.

8. The method of claim 1, wherein the mammal is a human.

9. The method of claim 1, wherein the Arenavirus is selected from the group consisting of Lassa, Junín, Machupo, Guanarito, Sabia, Whitewater Arroyo, Chapare, LCMV, and LCMV-like viruses.

10. The method of claim 9, wherein said LCMV-like viruses are selected from the group consisting of Dandenong, Tacaribe, and Pichinde.

11. The method of claim 1, wherein said viral infection is associated with a condition selected from the group consisting of viral hemorrhagic fever, meningitis, meningoencephalitis, encephalitis and arenavirus-mediated disease in organ transplant recipients.

12. The method of claim 1, wherein said viral infection is associated with birth defects and natural abortions.

13. The method of claim 1, which further comprises co-administration of at least one agent selected from the group consisting of antiviral agent, vaccine, and interferon.

14. The method of claim 13, wherein said antiviral agent is Ribavirin.

15. The method of claim 13, wherein said interferon is pegylated.

16. A method of inhibiting or causing regression of an Arenavirus infection, comprising administering in a therapeutically effective amount to a mammal in need thereof, a 1H, 1'H-[2,2']bibenzoimidazolyl.

17. A method of inhibiting or causing regression of an Arenavirus infection, comprising administering in a therapeutically effective amount to a mammal in need thereof, a 4,4'-Difluro-1H, 1H'-[2,2']bibenzoimidazolyl.

18. A method of inhibiting or causing regression of an Arenavirus infection, comprising administering in a therapeutically effective amount to a mammal in need thereof, a 4,6,4',6'-Tetrafluoro-1H, 1'H-[2,2']bibenzoimidazolyl.

* * * * *